US00PP09123P

United States Patent [19]

Goffreda et al.

[11] Patent Number: Plant 9,123

[45] Date of Patent: May 2, 1995

[54] APPLE TREE NJ109

[75] Inventors: Joseph C. Goffreda, Kendall Park; Anna M. Voordeckers, East Windsor, both of N.J.

[73] Assignee: Rutgers University, New Brunswick, N.J.

[21] Appl. No.: 235,855

[22] Filed: Apr. 29, 1994

[51] Int. Cl.[6] ..... A01H 5/00

[52] U.S. Cl. ..... Plt./35.1

[58] Field of Search ..... Plt. 35.1

*Primary Examiner*—James R. Feyrer

*Attorney, Agent, or Firm*—Synnestvedt & Lechner

[57] ABSTRACT

This invention relates to a new cultivar of apple tree named 'NJ109' which was created by crossing 'Golden Delicious' (as the seed parent) with 'NJ88' (as the pollen parent), and is characterized by its early ripening, attractive appearance, and very good dessert quality.

2 Drawing Sheets

BACKGROUND AND SUMMARY OF THE INVENTION

This invention is a new and distinct cultivar of apple tree that has been given the variety name or denomination 'NJ109'.

The new variety was discovered by applicants in September 1980, in the course of their work in connection with an ongoing breeding program seeking to develop improved early-maturing apple trees with improved fruit quality.

The new cultivar 'NJ109' is a seedling produced from crossing the cultivar 'Golden Delicious' (an unpatented variety) as the seed parent and the selection 'NJ88' (an unpatented variety) as the pollen parent. The cross was made in 1971 at the Horticulture Research Farm No. 2, New Brunswick, N.J.

In 1972 the seedling was transplanted to Block D at the Rutgers Fruit Research and Development Center, Cream Ridge, N.J. In the above orchard, its position was Row 100, Tree 156, having the description D-100-156 in the breeding records.

The new tree of this invention, 'NJ109', had as its seed parent the variety 'Golden Delicious', and as its pollen parent 'NJ88'. The pollen parent, which is no longer available, was a product of 'Golden Delicious' × 'M2439'. The parentage of 'M2439', was 'Crown Prince Rudolf' × 'James Grieve'. All specimens of the pollen parent of 'NJ109' have been destroyed, and notes to its characteristics are almost nonexistent.

In September 1980 after several years of observing the growth and characteristics of the seedlings under study at Cream Ridge, applicants selected the cultivar now known as 'NJ109' for further study and they asexually propagated the cultivar by grafting it on M7a dwarfing rootstock. Subsequently, applicants determined that the grafted material maintained the desired and distinguishing characteristics after propagation over several generations.

The new cultivar produces a moderately vigorous, spreading tree. Fruit is numerous and borne uniformly throughout the tree canopy on short axillary branches. The tree flowers over a prolonged period with the majority of flowers opening a few days before the cultivar 'Golden Delicious'. The apple fruit is attractive and possesses a crisp texture.

BRIEF DESCRIPTION OF THE FIGURES

In order to support the disclosure herein, there is provided a drawing wherein.

Figure 1:
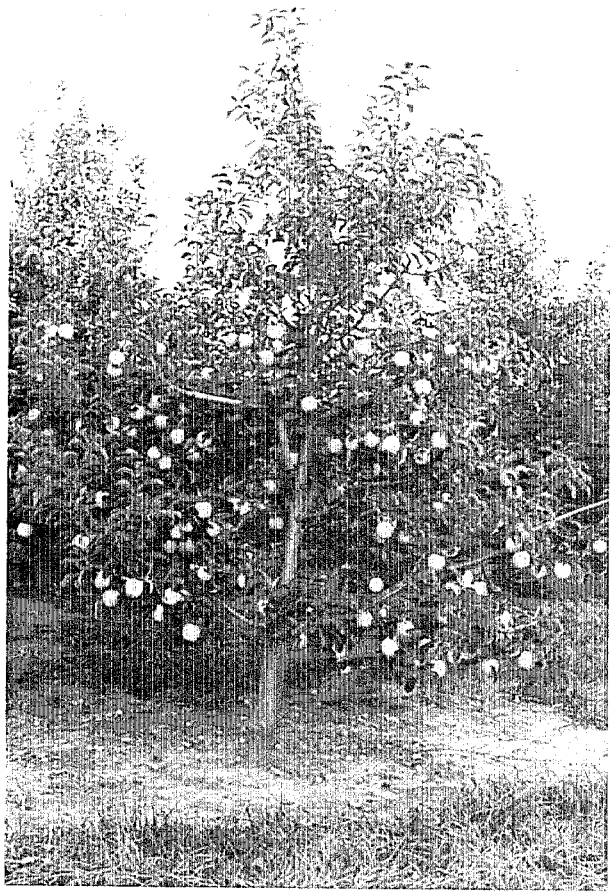
FIG. 1 shows a typical example of young tree of the new cultivar illustrating the growth habit thereof at or about the time when picking would normally be effected.
Figure 2:
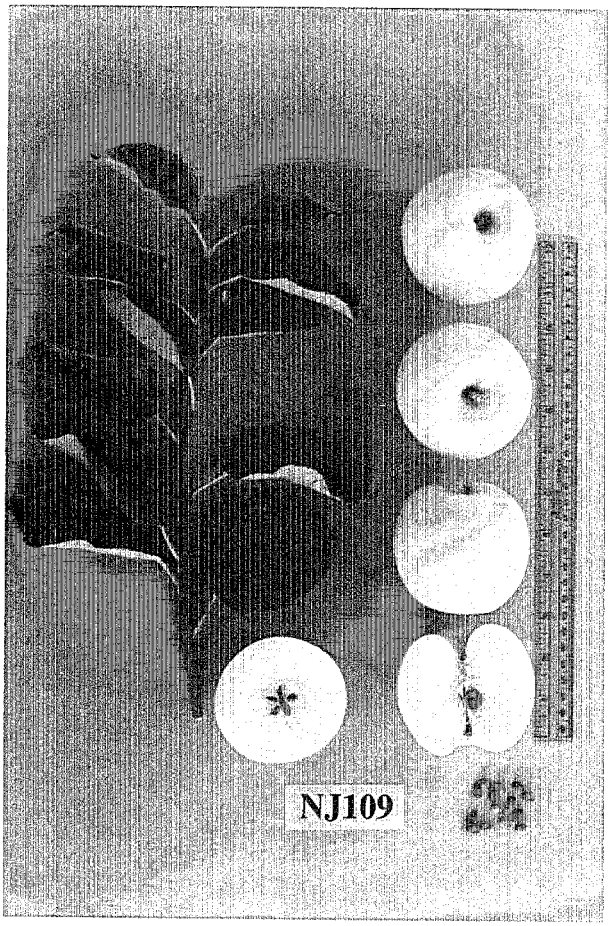
FIG. 2 shows a typical example of the apple fruit, seeds, and leaves produced, disclosing the fruit's color, round-oblong shape, flesh color, and skin color, and the leaf and seed shape.

The accompanying drawings are color photographs of the actual fruit and tree.

DETAILED DESCRIPTION OF THE PLANT

In order to describe the tree and fruit in particular detail, reference is had to a color chart, known as The Horticultural Colour Chart issued by The British Colour Council in collaboration with The Royal Horticultural Society. Throughout this specification, color names beginning with a small letter signify that the name of the color, as used in common speech, is aptly descriptive. Color means beginning with a capital letter designate color values based on The Horticultural Colour Chart.

Color was also measured in terms of its color space coordinates (L*a*b*) with a Minolta CR-300 Chroma Meter calibrated with a white calibration plate.

Turning to a consideration of the details of this new cultivar 'NJ109', we note that the following description is a detailed description of the tree grown in South Central New Jersey and of the fruit produced thereby. It describes the principal distinctive characteristics and identifying criteria by which the tree is recognized and the fruit produced thereby can be distinguished from known apple tree varieties. It is believed that the tree grown under comparable conditions and the fruit thereof will closely conform to the description.

FLOWER

Petals: 2.9 cm (range 2.5–3.3 cm) in length and 1.9 cm (range 1.5–2.1 cm) in width.

Corolla: 5.1 cm (range 4.6–5.6 cm) in diameter at near petal fall.

Color: Flower buds are Ruby Red to Magenta Rose between Plates 64a and 64b; fading to white, open flowers.

Bloom Dates: Blooms between April and early May in South, Central New Jersey; flowers over a prolonged period, as compared to 'Golden Delicious'.

Pollinaton: Most apple trees which bloom mid-season are most probably effective pollinizers for 'NJ109'.

FRUIT

Shape: Round-oblong; uniform.

Size: Axial diameter 7.1 cm (range 6.7–7.8 cm); transverse diameter 7.8 cm (range 6.6–8.3 cm).

Color: Undercolor is Barium Yellow (between Plates 10b to 10c; $L^*=76.85$ $a^*=-8.71$ $b^*=+43.27$). A faint orange blush will develop on 0–25% of exposed surfaces.

Skin: Smooth, with many small light brown dots (lenticels) distributed evenly on the fruit, very slightly raised; skin thickness medium-thin.

Stem: Length medium, 2.0 cm (range 1.8 to 2.3 cm), thickness medium to thick.

Cavity: Acuminate, very deep, medium in width, slight russet.

Basin: Deep, slightly furrowed, wide in breadth.

Calyx: Persistent, connivent (closed).

Calyx tube: Medium length and width, funnel shape.

Stamen remnants: Median.

Core: Median position.

Core lines: Clasping, distinct.

Carpels: Axile, open in cross section; obovate in longitudinal section.

Seeds:

*Shape.*—Acute, plump, not tufted.

*Average number per fruit.*—12.35.

*Average length.*—10.65 mm (0.43 in).

*Average width at widest point.*—4.13 mm (0.17 in).

*Color (dry seed coat).*—Beech Brown (Plate 165a)

Flesh:

*Texture.*—Medium, crisp, breaking.

*Quality.*—Sweet, mild subacid, very good dessert quality.

*Color.*—Naples yellow (Plate 11c).

*Aroma.*—Slight.

Maturity:

*Time of ripening.*—3–4 weeks before 'Golden Delicious'; although fruit ripens uniformly, it maintains firmness and texture, and consequently can be picked over an extended period (a single harvest may be all that is necessary).

*First picking date.*—Aug. 21–30 in South, Central New Jersey.

Keeping quality: Average, retains quality and texture for at least 2 months in refrigerated storage at 34° F.

Use: Early maturing, golden-type, dessert apple.

TREE

Tree: Moderately vigorous, spreading, very productive and produces annually. When grafted on M7a rootstock (a dwarfing rootstock) the tree is smaller and more precocious than when the tree is on its own roots that are nearly equivalent to "standard rootstock." Other than tree size, the fruit characteristics are maintained on the M7a rootstock.

LEAVES

Average size: Length 8.9 cm (range 7.7–11 cm); width 5.5 cm (range 3.9–6.5 cm).

Length to width ratio: 1.6 (range 1.4 to 2.0).

Form: Ovate, apex acuminate to cuspidate, base obtuse.

Margin: Serrate with slightly rounded teeth.

Petiole: Average length 2.3 cm (range 2.1 to 2.7 cm).

Color: Leaf color is strongly influenced by the environment (time of year, nitrogen levels in the soil, rootstock, etc.) and develops various shades of green.

We claim:

1. A new and distinct apple tree cultivar, substantially as herein shown and described.

* * * * *